United States Patent [19]

Koontz et al.

[11] Patent Number: 5,369,012
[45] Date of Patent: Nov. 29, 1994

[54] METHOD OF MAKING A MEMBRANE HAVING HYDROPHILIC AND HYDROPHOBIC SURFACES FOR ADHERING CELLS OR ANTIBODIES BY USING ATOMIC OXYGEN OR HYDROXYL RADICALS

[75] Inventors: Steven L. Koontz, Seabrook; Glenn F. Spaulding, Houston, both of Tex.

[73] Assignee: The United States of America as represented by the Administrator of the National Aeronautics and Space Administration, Washington, D.C.

[21] Appl. No.: 857,901

[22] Filed: Mar. 26, 1992

[51] Int. Cl.$^5$ .............. G01N 33/545; G01N 33/535; C12N 11/08; C12N 5/00

[52] U.S. Cl. .................. 435/7.92; 435/180; 435/181; 435/240.23; 435/240.243; 436/531; 436/532; 530/815; 530/816

[58] Field of Search ............ 435/7.92, 174, 180, 435/181; 436/531, 532; 530/815, 816

[56] References Cited

U.S. PATENT DOCUMENTS

| | | | |
|---|---|---|---|
| 4,143,949 | 3/1979 | Chen | 351/160 H |
| 4,440,853 | 4/1984 | Michaels et al. | 435/182 X |
| 4,778,471 | 10/1988 | Bajpai | 623/16 |
| 5,026,650 | 6/1991 | Schwarz et al. | 435/286 |
| 5,141,806 | 8/1992 | Koontz | 530/413 |

OTHER PUBLICATIONS

Shekachi, et al., Journal of Clinical Microbiology, vol. 16, No. 6, 1982, pp. 1012–1018.
Tsai, Chi–Chun et al., Transactions of the American Society of Artificial Internal Organs (ASAIO), vol. XXXIV, (1988), "Enhanced Albumin Affinity of Silicone Rubber," pp. 559–563.
Tsai, Chi–Chun et al., Transactions of the American Society of Artifical Internal Organs (ASAIO), vol. XXXVI, (1990), "Biocompatible Coatings with High Albumin Affinity," pp. 017–019.
C. Stimpson et al., Biomaterials, Artificial Cells, and Artifical Organs, 17(1), (1989("Patency and Durability of Small Diameter Silicone Rubber Vascular Protheses." pp. 31–43.
Durrani et al., Polymer Surfaces and Interfaces, Chapter 10, J. Wiley and Sons, (1987), "Modification of Polymer Surfaces for Biomedical Applications," pp. 189–200.
Rajender Sipehia, Biomaterials, Artifical Cells, and Artifical Organs, 16(5), (1988–89), "FTIR ATR Spectra of Protein a Immobilized on to Functionalized Polypropylene Membranes by Gaseous Plasma of Oxygen and of Anhydrous Ammonia", pp. 955–966.
Rajender Sipehia, Biomaterials, Artifical Cells, and Artifical Organs, 18(3), (1990), "The Enhanced Attach- (List continued on next page.)

Primary Examiner—David M. Naff
Attorney, Agent, or Firm—Hardie R. Barr; Guy M. Miller; Edward K. Fein

[57] ABSTRACT

A portion of an organic polymer article such as a membrane is made hydrophilic by exposing a hydrophobic surface of the article to a depth of about 50 to about 5000 angstroms to atomic oxygen or hydroxyl radicals at a temperature below 100° C., preferably below 40° C., to form a hydrophilic uniform surface layer of hydrophilic hydroxyl groups. The atomic oxygen and hydroxyl radicals are generated by a flowing afterglow microwave discharge, and the surface is outside of a plasma produced by the discharge. A membrane having both hydrophilic and hydrophobic surfaces can be used in an immunoassay by adhering antibodies to the hydrophobic surface. In another embodiment, the membrane is used in cell culturing where cells adhere to the hydrophilic surface. Prior to adhering cells, the hydrophilic surface may be grafted with a compatibilizing compound. A plurality of hydrophilic regions bounded by adjacent hydrophobic regions can be produced such that a maximum of one cell per each hydrophilic region adheres.

10 Claims, 1 Drawing Sheet

OTHER PUBLICATIONS ment and Growth of Endothelial Cells on Anhydrous Ammonia Gaseous Plasma Modified Surfaces of Polystyrene and Poly(Tetrafluoroethylene)," pp. 437–446.

Elizabeth G. Nabel et al., Science, vol. 244, 16 Jun. 1989, "Recombinant Gene Expression in Vivo Within Endothelial Cells of the Arterial Wall," pp. 1342–1346.

Hiroo Iwata et al, Journal of Membrane Science, vol. 38, (1988), "Preparation and Properties of Novel Environment–Sensitive Membranes Prepared by Graft Polymerization onto a Porous Membrane," pp. 185–199.

J. Wolff, Journal of Membrane Science, vol. 36, (1988), "Tailoring of Ultrafiltration Membranes by Plasma Treatment and Their Application for the Desalination and Concentration of Water–Soluble Organic Substances," pp. 207–214.

F. Vigo et al, Journal of Membrane Science, vol. 36, (1988) "Poly (Vinyl Chloride) Ultrafiltration Membranes Modified by High Frequency Discharge Treatment," p. 187.

F. F. Stengaard, Journal of Membrane Science, vol. 36, (1988), "Preparation of Asymmetric Microfiltration Membranes and Modification of Their Properties by Chemical Treatment," p. 257.

Fang Yuee et al., Journal of Membrane Science, vol. 39 (1988), "Polypropylene Dialysis Membrane Prepared by Cobalt–60 Gamma–Radiation–Induced Graft Copolymerization," pp. 1–9.

H. K. Yasuda et al., Polymer Sciences and Interfaces, Chapter 8, J. Wiley and Sons, 1987, "Plasma–surface Interactions in the Plasma Modification of Polymer Surfaces," pp. 149–162.

Attar S. Chawla, Artifical Organs, vol. 3 (1), (1979), "Use of Plasma Polymerization for Preparing Silicone–Coated Membranes for Possible Use in Blood Oxygenators," pp. 92–93.

Y. Ikada, Polymers in Medicine and Surgery, Plastics and Rubber Institute and Science and Technology Publishers, Hornchurch, UK, (1986), "Development of a Polymer Surface with non–Adherent Platelet Properties," pp. 6/1–6/8.

METHOD OF MAKING A MEMBRANE HAVING HYDROPHILIC AND HYDROPHOBIC SURFACES FOR ADHERING CELLS OR ANTIBODIES BY USING ATOMIC OXYGEN OR HYDROXYL RADICALS

ORIGIN OF THE INVENTION

The invention described herein was made by employee(s) of the United States Government of the United States of America for governmental purposes without the payment of any royalties thereon or therefor.

FIELD OF THE INVENTION

The present invention relates to a method for making biocompatible polymer articles using a uniform atomic oxygen treatment, and more particularly to polymer articles having a biocompatibilized surface comprising grafts of uniformly distributed compatibilizing compounds and a method for making such articles. The invention also relates to vascular prostheses having a biocompatibilized surface comprising a uniform distribution of living cells adhered thereto. The invention further relates to atomic oxygen modified membranes useful in medical diagnostic procedures and biochemical manufacture.

BACKGROUND OF THE INVENTION

The use of polymeric materials for biomedical implants and in biotechnical manufacture is an advancing art. Plasma discharges have been used to engineer such polymers because surface chemistry can be altered without adversely affecting bulk properties which make polymeric materials useful. However, plasma devices typically do not deliver a uniform concentration of the reactive species. Subject to complex interactions, non-uniform distribution of plasma species may increase manufacturing difficulty and impair quality control.

Silicone rubber has long been used in medical devices such as surgical implants due to desirable properties including gas permeability, pliability, degradation resistance, ease of fabrication and relatively good biocompatibility. However, such materials are not completely inert in the body. Recent methods have been sought to improve its biologic inertness by either surface modification to increase hydrophilicity or bulk modification, i.e. incorporating polar groups into the monomer or prepolymer. Tsai, Chi-Chun et al., in *Transactions of the American Society of Artificial Internal Organs* (ASAIO), vol. XXXIV, (1988) discloses a method for increasing the albumin affinity of silicone rubber. A vinyl-methyl silicone comonomer was hydroxylated and then film coated on a silicone rubber sheet. The OH-coated sheet was grafted with a $C_{16}$ alkyl chain having a terminal acyl group by an esterification reaction catalyzed by 4-dimethylaminopyridine. Albumin adsorption and retention was said to be markedly enhanced for surface OH and $C_{16}$ concentrations as low as 5% reaction yield. Tsai, Chi-Chun et al., in ASAIO, vol. XXXVI, (1990) discloses use of the above albumin adsorbed silicone surfaces as thin transparent, biocompatible films for coating the surfaces of blood contacting devices. These films are said to retard undesired responses, e.g. blood coagulation and activation of complement proteins, platelets and white blood cells, triggered by exposure of blood stream macromolecules to a foreign surface.

Polymer prostheses have been considered for vascular applications. C. Stimpson et al., in *Biomaterials, Artificial Cells, and Artificial Organs*, 17(1), (1989), pp. 31–43 discloses silicone rubber canine aortic prostheses. A uniformly microporous prosthesis is made by molding the polymer in a template taken from the skeletal structure of a marine life form.

Durrani et al., in *Polymer Surfaces and Interfaces*, chapter 10, J Wiley & Sons, (1987), pages 189–200 discloses modification of polymer surfaces with a phosphorylcholine, for example, to mimic biomembrane surfaces in bioapplications. Modifications of this sort are said to reduce foreign surface induced thromboses associated with the use of blood contacting devices.

Rajender Sipehia in *Biomaterials, Artificial Cells, and Artificial Organs*, 16(5), (1988–89), pp. 955–966 discloses immobilizing proteins to polymeric surfaces. Polypropylene membranes are treated by gaseous oxygen or ammonia plasma to add hydroxyl or amino groups to the polymer surface. The proteins are then grafted to the surface. Rajender Sipehia in *Biomaterials, Artificial Cells, and Artificial Organs*, 18(3), (1990), pp. 437–446 discloses ammonia plasma modification of polystyrene petri dishes and poly(tetrafluoroethylene) membranes and grafting of proteins to the surface. The growth of bovine pulmonary artery endothelial cells on the modified surface is enhanced by adherence to the grafted proteins.

In U.S. Pat. No. 4,134,949 to Chen, the surface of a contact lens is modified by deposition of a hydrophilic polymer under the influence of plasma glow discharge to integrally bond the coating to the surface of a hydrophobic lens.

Elizabeth G. Nabel et al., in *Science*, vol. 244, 16 Jun. 1989, pp. 1342–1345 discloses a transplant of endothelial cells expressing a recombinant gene into an arterial wall. The transplanted cells may contribute to altering the thrombic properties of the vessel lumen by inducing smooth muscle cell proliferation and regulating smooth muscle cell tone. In addition, genetically altered cells could transmit recombinant DNA products.

Polymer surfaces have been modified by plasma application to prepare membranes for dialysis and ultrafiltration. Hiroo Iwata et al. in *Journal of Membrane Science*, vol. 38, (1988), pp. 185–189 discloses a porous poly(vinylidene fluoride) membrane pretreated by air plasma and subsequent graft polymerization of hydrophilic monomers on the treated surface. Such membranes are said to be environment-sensitive and can be used to mimic biological membranes or in a closed-loop drug delivery system. J. Wolff, *Journal of Membrane Science*, vol. 36, (1988), pp. 207–214; F. Vigo et al., *Journal of Membrane Science*, vol. 36, (1988), pp. 187–199; F. F. Stengaard, *Journal of Membrane Science*, vol. 36, (1988), pp. 257–275; and Fang Yuee et al., *Journal of Membrane Science*, vol. 39, (1988), pp. 1–9 disclose the preparation of a variety of dialyses and ultrafiltration membranes.

Various polymers have been modified by plasma processes to alter surface chemistry, adhesion properties, and the like. See H. K. Yasuda et al., *Polymer Surfaces and Interfaces*, chapter 8, J Wiley & Sons, (1987), pages 149–162.

SUMMARY OF THE INVENTION

The method of the present invention is based on the discovery of an atomic oxygen treatment method capable of producing a substantially uniform concentration of reactive atomic oxygen species. Polymer substrates so treated have a uniform distribution of hydrophilic functionality on the treated surface. Such functionality is useful for biocompatibilizing polymer articles for biomedical and biotechnical applications.

In one embodiment, the present invention provides a biotechnical method, comprising the steps of: (a) exposing a hydrophobic exterior polymer surface to a substantially axially uniform dosage of atomic oxygen or hydroxyl radicals at a temperature below about 100° C. sufficient to form a uniform layer of hydrophilic hydroxyl radically on said surface, wherein the dosage is generated by a flowing afterglow microwave discharge, wherein the surface is outside of a plasma produced by the discharge; and (b) recovering a biocompatible article. The method may further comprise the steps of grafting a compatibilizing compound to the surface following the exposing step and adhering a layer of living cells to the compatibilizing compound. The grafting step may include the preliminary step of treating the surface with a dihalodialkylsilane coupling agent. The compatibilizing compound is preferably selected from the group consisting of bioactive compounds such as phosphorylcholines, peptide sequences, lipids and proteins; polymers such a poly(ethylene oxide) and poly(vinyl alcohol); and compounds comprising acyl terminated upper alkyl radicals. The dosage over the exposed surface preferably comprises a concentration within about 10 percent of an average dosage over the surface and is essentially free of atomic oxygen dose variation in a radial direction. As one preferred aspect, the method of the invention can be used to vascularize a cell mass wherein a prosthesis is prepared from a polymeric tube having an outside surface biocompatibilized with an adhered layer of cells as described above and then inserting the prosthesis into the cell mass. In general, an implantable article can be prepared by appropriately treating membranes, tubes or molded forms.

As another preferred aspect, the method of the invention can be used to conduct an enzyme-linked immunosorbent assay test. A membrane having a hydrophilic surface and a hydrophobic surface is prepared as described above. Known antibodies are adhered to the hydrophobic surface. Then the hydrophilic surface is placed in contact with an adjacent absorbent material. The antibodies are covered with a test solution, wherein antigens specific to the antibodies adhere thereto to form an antibody-antigen complex and the non-compatible antigens are absorbed by the absorbent material. The hydrophobic surface is covered with a solution of the antibodies conjugated to an indicating enzyme, wherein the conjugated antibodies and the antigen-antibody complex form an antibody-antigen-antibody/enzyme complex and excess fluid is absorbed by the absorbent material. The antibody-antigen-antibody/enzyme complex are developed with a solution of developing compound reactive with the enzyme to indicate presence of the antibody-antigen-antibody/enzyme complex as a positive result or an absence of the complexes as a negative result, wherein excess developing solution is absorbed by the absorbent material.

As a further preferred aspect, the method of the invention can be used to culture cells for malignant cell evaluation. A membrane is prepared having a surface comprising a plurality of hydrophilic regions bounded by hydrophobic regions as described above. A group of cells are distributed on the membrane in a growth medium, wherein the cells adhere to the hydrophilic regions at a maximum density of one cell per each hydrophilic region and hydrophobic regions are substantially free of adhered cells. The cells are grown on the membrane and a count of malignant cells growing on the membrane cells is obtained.

As yet another preferred aspect, the method of the invention can be used to culture cells with enhanced recovery of biological products. A membrane with first and second opposing surfaces is prepared wherein the first surface comprises a hydrophilic area bounded by a hydrophobic area as described above. Cell culturing and product compartments are formed separated by the membrane, wherein the first membrane surface is adjacent the cell culturing compartment and the second membrane surface is adjacent the product compartment, the cell culturing compartment comprising cells in a growth medium, the cells having a gene for the expression of a desired product. The cells are induced to adhere to the hydrophilic area of the first surface of the membrane, wherein the cells polarize with a basal cell wall adjacent the first surface. Nutrient migration is induced from the nutrient compartment to the cells compartment by maintaining nutrient in the cell culturing compartment, wherein the cells absorb the nutrient and in response thereto secrete a product preferentially through the basal cell wall and the membrane into the product compartment.

As yet a further preferred aspect, the method of the invention can be used to culture cells with self-replenishing nutrients. A membrane is prepared with a first hydrophobic surface and a second hydrophilic surface as described above. A nutrient compartment and a cells compartment are formed on opposite sides of the membrane, wherein the second surface is adjacent the nutrient compartment and the first surface is adjacent the cells compartment, the nutrient compartment comprising a solution of nutrient and the cells compartment comprising cells in a growth medium. Migration is induced of said nutrient from said nutrient compartment to said cells compartment by maintaining a concentration of said nutrient in said nutrient compartment.

In another embodiment, the invention provides biotechnical polymer articles suitable for use in biomedical or biotechnical applications, comprising at least one surface biocompatibilized at least in part by the method described above. The biocompatibilized surface can comprise a substantially uniform distribution of reactive hydrophilic functionality, a compatibilizing compound grafted to the surface using the hydrophilic functionality and/or a layer of living cells adhered to the surface using the hydrophilic functionality and/or the compatibilizing compounds. Examples of such articles include vascular prostheses, membranes, dressing textiles, molded implants having surfaces inhibiting platelet adhesion and articles having surfaces enhancing cell adhesion.

In a further embodiment, the invention provides a bioreactor comprising a housing; a membrane having at least a portion of one biocompatibilized surface made by the method described above dividing the housing into an opposing nutrient compartment and product compartment; and cells in a growth medium in the nutrient compartment.

DETAILED DESCRIPTION OF THE INVENTION

Figure 1:
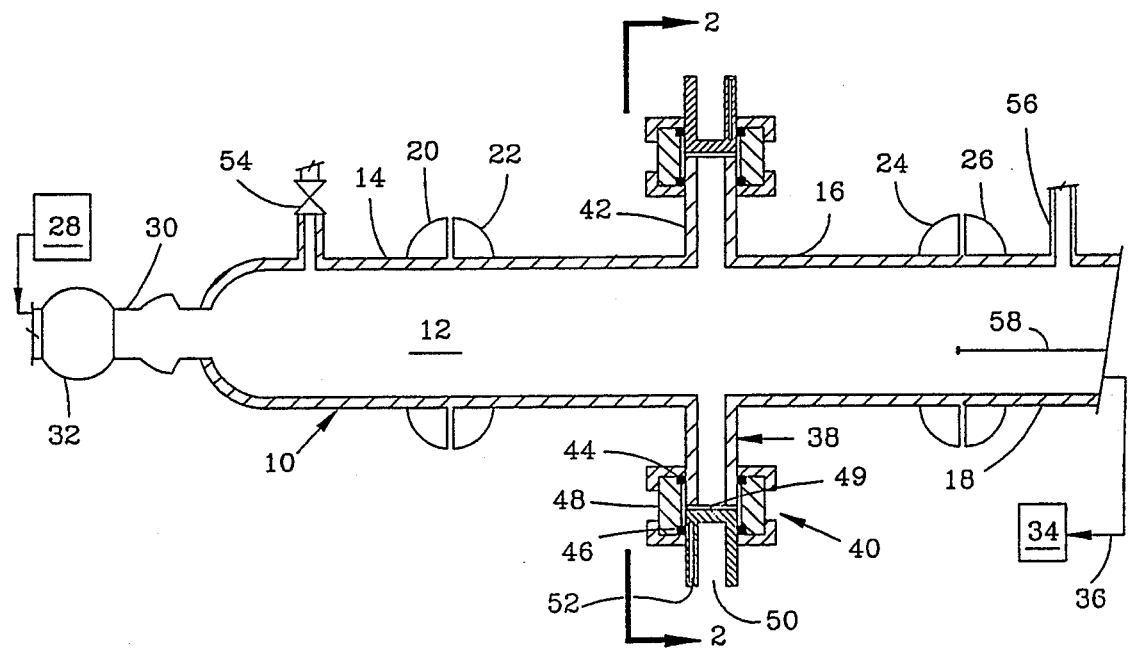
FIG. 1 is a schematic cross-sectional representation of a sidearm afterglow atomic oxygen reactor suitable for use in the present invention.

A substantially uniformly compatiblized polymer article for a biologic environment, i.e. in the presence of bioactive molecules, can be obtained by treating a sufficient amount of surface of the article with a substantially uniform concentration of an oxidizing plasma species, then optionally grafting compatibilizing compounds to the treated surface. In addition, the grafted substrate may be used as a base for succeeding grafts or as an adhesive layer for proteins or living cells.

In one aspect, a hydrophobic polymer substrate may be treated with a substantially uniform concentration of atomic oxygen or hydroxyl radicals to form a substantially uniform hydrophilic surface layer on the substrate. The hydrophilic surface substantially comprises reactive hydroxyl functionality. A hydrophilic surface may be used to enhance water wettability of the substrate, enhance surface adsorption of proteins or other bioactive compounds, enhance surface adherence of cells or as a base for further surface compatibilizing grafting reactions.

As another aspect, the substantially hydrophobic surface layer may made to undergo one or more modifications in a series of chemical reactions to graft a compatibilizing compound to the substrate surface. Various kinds of compatibilizing compounds are contemplated and may be used so long as the result is a substrate more compatible with the biologic environment of the application involved. By "compatibilizing," it is meant that an otherwise non-biologic surface, e.g. hydrophobic polymer surface, is made more like known biologic surfaces to a substantial but varying degree. The compatibilizing compound may be bioactive, i.e. found in life processes or non-bioactive but serve to compatibilize the substrate in situ. Representative examples of bioactive compounds which may be used include compounds having phosphoryl-choline functionality, peptide sequences, proteins, lipids, nucleic acids, and the like. Substrates with protein or other bioactive grafts have several compatibilizing applications. One important use is preventing thrombosis around an implanted article by mimicking biologic surfaces. As another use, grafted proteins may serve as an adherent or adsorbent for cultured cells.

Other compounds which have been found to have a compatibilizing use include polymeric groups such as poly(vinyl alcohol) and poly(ethylene oxide); and an acyl terminated upper alkyl radical such as an acyl terminated alkyl radical of about 16 carbon atoms. The former have been found to inhibit platelet sticking in the blood stream, see Y. Ikada, "Development of a Polymer Surface with anti-adherent Platelet Properties" compiled in *Polymers in Medicine and Surgery*, Plastics and Rubber Institute Science and Technology Publishers, Hornchurch, UK, 1986 which is hereby incorporated herein by reference. The latter has been found to have enhanced affinity for blood proteins such as albumin. This albumin layer inhibits clotting at the compatibilized surface. See Tsai, Chi-Chun et al., ASAIO, vols. XXXIV (1988) and XXXVI (1990) which are hereby incorporated herein by reference.

As a further aspect, a substrate comprising a protein grafted polymer surface can have living cells such as endothelial cells adhered to the protein grafts. Furthermore such cells can be genetically altered to transmit recombinant DNA products. Such substrates can be utilized in vascular, skeletal, and the like prostheses; as a vascular network for microgravity cell culturing processes; or in earth-based bioprocessing methodology, e.g. affinity columns. Vascular prostheses can be used in persons suffering advanced arteriosclerosis.

To limit oxidation the outer portion of the substrate and avoid altering the bulk properties of the polymer, highly reactive atomic oxygen or hydroxyl radicals are preferred oxidizing agents. Atomic oxygen has the advantage over molecular oxygen of obtaining a distinct oxidation front, generally on the order of a molecular diameter, i.e. from about 50 to about 5000 angstroms. In addition, atomic oxygen does not require the high temperatures that thermal, molecular oxygen requires, so there are no thermally induced changes in the physical or structural characteristics of the polymer when the atomic oxygen is used at a low temperature, preferably below about 100° C., and more preferably below about 40° C.

To obtain uniform treatment of the substrate, a flowing afterglow discharge type atomic oxygen reactor is generally required. The surface of the article to be treated should be out of the plasma and the reactor configured to deliver a relatively uniform dose of oxygen atoms. The specific design of the flowing afterglow device will depend, of course, on the shape of the polymer article using the well known principles of diffusion/reaction kinetics in flowing systems.

Figure 2:
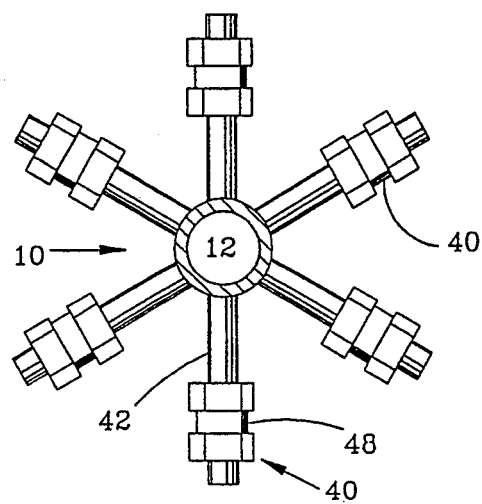
FIG. 2 is a schematic cross-sectional view of the sidearm atomic oxygen reactor of FIG. 1 as seen along the lines 2—2.

As a specific example, a side-arm reactor designed to provide a uniform dose of oxygen atoms to several disk shaped polymer samples is described. A suitable reactor 10 preferably having a sidearm 12 is best seen in FIG. 1. Reactor 10 is particularly useful for uniformly treating substrates having relatively large flat surfaces where it is also necessary to obtain a uniform depth of reaction with atomic oxygen across the surface. The sidearm atomic oxygen reactor 10 has a longitudinally oriented flow chamber 12 which may be appropriately constructed of glass or another suitable material in sections, e.g. inlet section 14, mid section 16 and discharge section 18, which are conveniently secured together using conventional coupling flanges 20, 22, 24 and 26. A gas flow source 28 supplies gas through inlet line 30 into the inlet section 14 of the chamber 12. A discharge generating apparatus 32 is positioned in the line 30 to generate a discharge in the gas flowing therethrough. A microwave power supply operation at 2450 Mhz, such as that obtained under the trade designation Ratheon PGM-10, used with an Evanson-type discharge cavity, has been found to be suitable for this purpose. The gas entering the chamber 12 in the inlet section 14 flows axially therethrough and is discharged from the discharge end 18 via line 36 in fluid communication with a vacuum pump 34. A plurality of sidearms 38 are positioned on the mid section 16 transversely to the longitudinal axis thereof (see FIG. 2). The sidearms 38 are preferably radially symmetrical and six sidearms 38 are illustrated here for the purposes of example, but any number more or less than six may be suitably used. A specimen holder 40 is positioned at a distal end of each sidearm conduit 42. The specimen holder 40 may be made, for example, by modifying a conventional union fitting such as a CAJON brand union, drilled through to remove internal lips and to include the O-ring vacuum seals 44, 46 at either end of a sleeve member 48 adjacent the conduit 42, so that disc-shaped specimen 49 can be held therein. If desired, each specimen holder may also include specimen heater well 50 and thermocouple well 52. Alternately, the specimen holder 40 may be provided with an adjusting mechanism to vary the distance of the specimen from the sidearm entrance, for example, using an insert (not shown) slideably engaged in the conduit 42. It is understood that while a specimen holder suited for a small disc-shaped article is shown, the holder design will depend upon shape and size of the article to be treated. The chamber 12 may further optionally include conventional sampling and probing means and apparatus, such as, for example, an $NO_2$ supply and metering valve connected at 54 onto inlet section 14 of the chamber 12, a capacitance manometer connection 56 on the discharge section 18, catalytic atomic oxygen probe 58 positioned adjacent the sidearm 38, and the like.

The sidearms 38 are constructed and operated so that no significant radial concentration gradients exist and a uniform atomic oxygen dose is thereby delivered to the substrate surface 49 which is held or secured transversely in the specimen holder 40.

The elimination of radial concentration gradients in the sidearms 38 is determined by the relative magnitude of two characteristic relaxation times, $T_{diff}$ and $T_{rcm}$ wherein $T_{diff}$ is the characteristic diffusional relaxation time for the sidearm 38 and $T_{rcm}$ is the time required for all atomic oxygen in the sidearm to recombine. When $T_{diff}$ is much less than $T_{rcm}$, then no significant radial concentration gradients exist and a uniform atomic oxygen dose is delivered to the substrate surface. $T_{diff}$ is determined according to the equation:

$$T_{diff} = R^2/D$$

Wherein R is the diameter of the side arm conduit and D is the atomic oxygen diffusional coefficient (about 120 cm$^2$/s in air at 65 Pa). $T_{rcm}$ is determined according to the equation:

$$T_{rcm} = R/r_c v$$

wherein $r_c$ is the fraction of oxygen atoms which recombine upon striking the sidearm surface (about $3.2 \times 10^{-4}$ in the case of glass) and v is the mean thermal speed of oxygen atoms (about $6.3 \times 10^4$ cm/s at 300° K.). Thus, when R=1 cm and the reactor is operated at 65 Pa and 300° K., $T_{diff}$ is about 0.008 seconds and Trcm is about 0.1 seconds. Thus, the side-arm reactor can be used to provide a predetermined, uniform dose rate of atomic oxygen across the substrate surface, avoiding complications resulting from the effects of boundary-layer mass transfer which are substantially absent in the present device.

As an example, an atomic oxygen concentration in the gas chamber at the entrance to the side arm conduit of about $1 \times 10^{16}$ atoms/cm$^3$, or about 5 percent of the flowing gas at 65 Pa, can be produced using conventional atomic oxygen production. Higher atomic oxygen concentration in the gas chamber would obtain higher dose rates, and lower pressure, e.g. 13 Pa of lower would tend to also increase atomic oxygen dose rate, as well as the diffusion constant (which would increase the value of $T_{diff}$).

The atomic oxygen dose rate can be estimated by analytical solution of the partial differential equation describing the diffusional transport and first order or pseudo first order reaction processes for cylindrical geometry reactors:

$$k_c C(r,z) = D \frac{1}{r \partial r} \frac{\partial}{\partial r} r C(r,z) + \frac{\partial^2}{\partial z^2} C(r,z)$$

wherein $k_c$ is the rate constant for atomic oxygen loss in the sidearm conduit from all first order processes, C is the atomic oxygen concentration, r is the radial position from the longitudinal axis of the sidearm conduit, and z is an axial position (distance from the sidearm conduit entrance from the main gas chamber), with the boundary conditions:

$$C(r,z) = C_0, \text{ at } z = 0;$$
and $$-D \frac{\partial}{\partial z} C(r,z) = k_s C(r,z), \quad \text{at } z = z_1 \quad ;$$
(the specimen surface)

wherein $k_s$ is the rate constant for atomic oxygen loss at the specimen surface. If $T_{diff} << T_{rcm}$ the partial differential equation simplifies to:

$$\frac{k_c C(z)}{D} = + \frac{\partial^2}{\partial z^2} C(z).$$

The complete analytical solution for the case of no radial dependence and first order atomic oxygen loss processes is as follows:

$$C(z) = \frac{C_0}{(G_A + G_B)} \{[G_B \exp[-(k_c/D)^{0.5} z] + G_A \exp[(k_c/D)^{0.5} z]\}$$

wherein constants $G_A$ and $G_B$ based on the above boundary conditions are:

$$G_A = [D(k_c/D)^{0.5} - k_s] \exp[-(k_c/D)^{0.5} z_1]; \text{ and}$$

$$G_B = [-D(k_c/D)^{0.5} + k_s] \exp[(k_c/D)^{0.5} z_1]$$

The atomic oxygen dose rate can thus be estimated, and it is readily appreciated that the dose rate can be increased dramatically by increasing the atomic oxygen concentration at the sidearm conduit entrance (at z=0), and altered by the material of the sidearm conduit and substrate.

Total atomic oxygen dose of about $10^{24}$–$10^{26}$ cm$^{-2}$day$^{-1}$ or more may be typically obtained. The affected substrate preferably receives an atomic oxygen dosage within about 10 percent of the average dosage.

As an intermediate step, a silane coupling agent may be used to graft the compatibilizing compound to the substrate surface. Such silane grafting reactions are known. Generally, the coupling agent comprises a suitable functional group which may be grafted to the substrate surface. The grafted functional group may be made to undergo subsequent chemical reaction with an appropriate compatibilizing compound. Alternatively, the silane couping agent is attached to the compatibilizing compound first.

One class of suitable silane coupling agents has the formula:

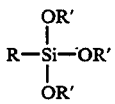

wherein R' independently comprises lower alkyl radicals or hydrogen, R comprises R"—Y wherein R" comprises lower alkyl radicals and Y is selected from the group consisting of terminal amino, mercapto, hydroxy, alkoxy, glycido and carboxy functionality. Representative examples include 3-aminopropyltris-(methoxy)silane, 3-mercaptopropyltris(methoxy)silane, 3-glycidopropyltris(methoxy)silane, 2-carboxyethyltris(ethoxy)silane, 4-hydroxybutyltris(propyloxy)silane, and the like. Another type silane coupling agent comprises dihalodialkylsilanes. Exemplary is dichlorodimethylsilane.

In addition, a first coupling agent grafted to the substrate or reacted with the compatibilizing compound may form an intermediate for a reaction with one or more additional coupling agents. Exemplary of such additional coupling compounds is tresyl chloride:

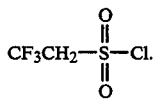

Tresyl chloride reacts with a terminal amino group in a glycine unit of a peptide sequence to couple the sequence to the underlying substrate.

The method of the present invention is suitable for use on most polymer substrates having inert hydrophobic surfaces. Such polymers are either carbon or silicon based. Representative examples of typical carbon-based polymers include polyolefins such as high and low density polyethylene and polypropylene, poly(ethyleneterephthalate), polyimides, polystyrene, polytetrafluoroethylene, poly(vinylidene fluoride), and the like. Examples of suitable silicon-based polymers include polydimethylsiloxane, polyphenylsiloxane, dimethylsiloxane/methylvinylsiloxane copolymer, crosslinked polysiloxanes obtained by hydrosilylation, condensation or free radical crosslinking of siloxane prepolymers or organosiloxane polymer mixtures, and the like.

Substrates may have most commonly known forms including textiles, tubes, films, membranes, sheets, molded forms, as well as composite films, membranes, textiles, and the like with other inert polymeric and non-polymeric materials used for reinforcement. As an example, a breathable, hydrophobic polysiloxane membrane reinforced with poly(tetrafluoroethylene) is sold under the tradename SILON by Bio-Med Sciences, Inc. This membrane is typically used as wound dressings, gas and fluid exchange membranes, etc.

Compatibilized articles made by the method of the invention find widespread use in biotechnical and biomedical application. By "biotechnical" it is understood to mean application to vitro processes. Examples of in vitro processes include manufacturing and purifying biocompounds such as lipids, complex carbohydrates, proteins and nucleic acids; preparing pharmaceutical chemicals used as drugs, drug intermediates, and the like; and cell culturing processes for drug manufacture, preparing organisms having altered genes, prostheses manufacture, and the like. "Biomedical" generally refers to vivo process application, i.e. extended contact with ongoing life processes.

The extent of compatibilization depends on the given application. Close compatibilization may duplicate the cell linings at the location of transplant. Lesser compatibilization may only require water wettability of a hydrophilic surface. Intermediate compatibilization may mimic a biologic substrate to a greater or lesser extent, enhance adsorption of biologic compounds such as albumin previously mentioned or prevent adhesion such as that of platelets to reduce unwanted clotting also previously mentioned. It is understood that a compatibilized substrate for an in vivo application is less likely to cause localize damage and/or irritation in an organism. An implant having compatibilized surfaces can last longer and is generally less likely to be rejected by the organism. A compatibilized substrate for an in vitro process will enhance the application and/or yield of the biotechnical process.

Representative examples of biomedical applications include contact lenses, dressings for enhancing the healing of skin, membranes for blood dialysis, prostheses for the vascular and skeletal system, artificial organs, implants for reconstructive and cosmetic surgery, implants for fighting disease, implants for regulating biological systems, implants for providing structural support for directing vascularization wherein the support frame implant is later removed, and the like.

Examples of biotechnical applications include gas and liquid separation membranes in the manufacture and/or purification of pharmaceutical compounds, chromatographic resins, improved cell culturing membranes and petri dishes, membranes for enhancing an evaluation rate of malignant cell growth, vascular conduits for microgravity cell culturing, diagnostic membranes for immune response testing, and the like.

Serological techniques such as enzyme-linked immunosorbent assay (ELISA) for determining the presence of antigens are enhanced by using a membrane wherein one surface is made hydrophilic by the method of the present invention. Successive sera liquids used by the ELISA test can be easily drawn through the membrane into an absorbent cotton or tissue paper using surface energy forces, thus avoiding undesirable washing steps which would otherwise be necessary. In such a manner, waste liquids can be more easily limited and confined. The hydrophobic side of the membrane is preferably used for the test reagent side and the hydrophilic side is set adjacent the absorbent paper to draw away the reagents and other test fluids from the test site. The ELISA test can be conducted using the modified membrane in either the "sandwich" method or the indirect method. The methods of the ELISA test are well known in the art.

Cell culturing techniques can be enhanced using polymeric membranes modified by the method of the present invention, especially for culturing cells that require anchorage to a hydrophilic surface to grow. Modified membranes having various hydrophilic/hydrophobic surface patterns can be made by masking the membrane before exposure to the atomic oxygen. Such modified membranes can be used as partitions in cell cultures. As one example, the membranes may be masked using a checkerboard stencil, and then modified by atomic oxygen treatment to form hydrophilic surface areas separated by hydrophobic boundaries. In a cell culture, each hydrophilic area comprises a separate microculture because cell growth is substantially confined to the hydrophilic area. Therefore, the hydrophilic "squares" typically have an area several times larger than the size of the cell to be grown. Cells cultured on the checkerboard membrane at an average density of about one cell per hydrophilic square or less form microcultures which can be used to greatly reduce the time and amount of materials required, for example, to make malignant cell growth evaluations of cells taken from tissue biopsies. A percentage of malignant growing cells can then be easily determined by observation of the whole.

Typically, tissue biopsy cells are evaluated for cancerous growth by culturing individual cells separately, and then observing the growth after a period of time. To insure no more than one cell per culture, the cells are ordinarily diluted serially using growth media to a concentration of about 0.6–0.8 cells per culture area. The less culture area required to differentiate between the cells, the less time and nutrients that are generally necessary for the evaluation. Typically, the area of the prior art evaluation cultures is about 0.25 $cm^2$.

Cell can be cultured in a vessel partitioned by a permeable membrane into compartments. Nutrients and/or products made by the culture may diffuse across the membrane. For example, a cell culture can be grown in a growth medium in a vessel wherein nutrients are self-replenished as used. The vessel is partitioned by a modified membrane of the present invention into dual compartments. The modified membrane has a hydrophobic surface and a hydrophilic surface. In one compartment adjacent the membrane hydrophobic surface, cells are cultured. The other compartment adjacent the membrane hydrophilic surface has growth medium. Nutrient diffusion from the nutrient compartment replenishes nutrients in the cells compartment as they are used.

Bioreactors partitioned by the modified membranes of the present invention as above can polarize the cells and thereby enhance production and separation of secreted biological products. Depending on the cells involved, polarization can occur in due course as cells adhere to a hydrophilic surface on the membrane and/or in response to a concentration gradient set up by a nutrient factor diffusing across the membrane. In either case, the cells define a basal cell wall adhered against the membrane partition and an opposite apical cell wall. The membrane of such bioreactors preferably has a hydrophobic surface adjacent a cell culture compartment except for an isolated hydrophilic area, such as, for example, a line or a strip for cell attachment. The other surface of the membrane adjacent a nutrient compartment can be hydrophobic or hydrophilic. Nutrients from the nutrient compartment diffuse through the membrane by concentration gradient to replenish nutrients used by the cells. Desired products made by the cells secrete through the basal cell wall and diffuse through the membrane partition into the nutrient compartment. In such manner, desired cell products can be recovered without lysing the cells.

The method of the invention is illustrated by the following examples:

Example 1

A polytetrafluoroethylene reinforced silicone membrane sold under the tradename SILON by Bio-Med Sciences, Inc. of Bethlehem, Pa. is uniformly treated with atomic oxygen in an atomic oxygen reactor having a specimen holding sidearm. Operating conditions are shown in the Table. The membrane initially has a hydrophobic surface which after treatment acquires hydrophilic hydroxyl functionality as follows:

| before | after |
|---|---|
| Surface | |
| $\begin{array}{c}CH_3\ CH_3\\|\ \ \ \ \ |\\(Si-O-Si)_n\\|\ \ \ \ \ |\\CH_3\ CH_3\end{array}$ + 18O $\rightarrow$ | $\begin{array}{c}OH\ \ OH\\|\ \ \ \ \ |\\(Si-O-Si)_n\\|\ \ \ \ \ |\\OH\ \ OH\end{array}$ + $6H_2O$ + $4CO_2$ |
| Sub-Surface | |
| $\begin{array}{c}CH_3\ CH_3\\|\ \ \ \ \ |\\(Si-O-Si)_n\\|\ \ \ \ \ |\\CH_3\ CH_3\end{array}$ | $\begin{array}{c}CH_3\ CH_3\\|\ \ \ \ \ |\\(Si-O-Si)_n\\|\ \ \ \ \ |\\CH_3\ CH_3\end{array}$ |

TABLE

| | |
|---|---|
| pressure (Pa) | 27 |
| temp (°K) | 298 |
| gas mixture | 10% $O_2$ in Ar |
| C(z) ($AO/cm^3$) | $4 \times 10^{14}$ |

Example 2

The membrane of Example 1 is reacted with a silane coupling agent to graft glycidyl functionality to the substrate surface. The grafting reaction proceeds as follows:

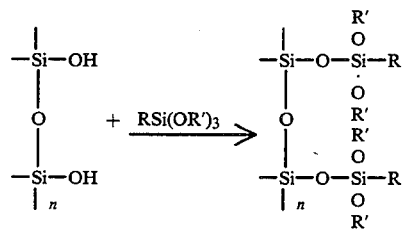

wherein R and R' are as previously defined.

3-Glycidylpropyltrismethoxysilane obtainable from Huls-Petrarch (item G6772) is dissolved in an ethanol/water solution (95 wt. % ethanol) to make a 1 wt. % solution of the glycidyl compound. The pH of the solution is adjusted to between about 4.5–5.5 with sodium acetate. The membrane from Example 1 is placed into the solution for 1–2 minutes then removed and rinsed with ethanol. After drying for 5–10 min at 110° C. or for 2.5 hrs in a desiccator, the membrane is used for further reaction.

Examples 3–4

Compatibilizing phosphorylcholine functionality is grafted to the surface of the membranes of Example 2 to mimic a cell membrane.

The membrane of Example 2 is stirred in a 40° C. water solution of ethyleneglycophosphorylcholine for 16 hours. The pH of the reaction medium is 4.5 to 6. The reaction is as follows:

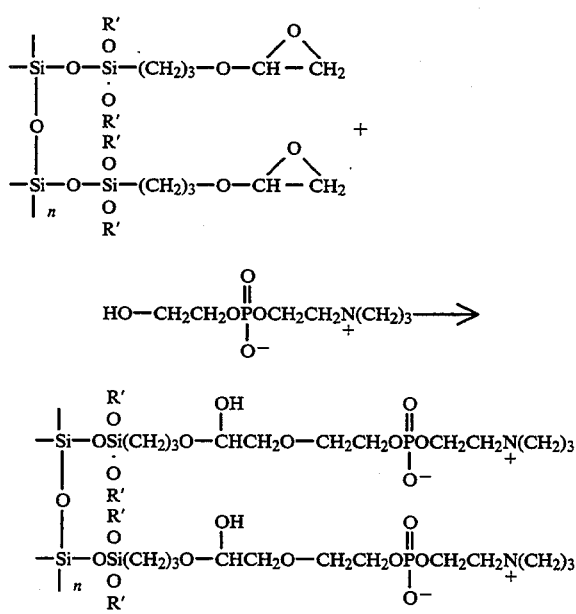

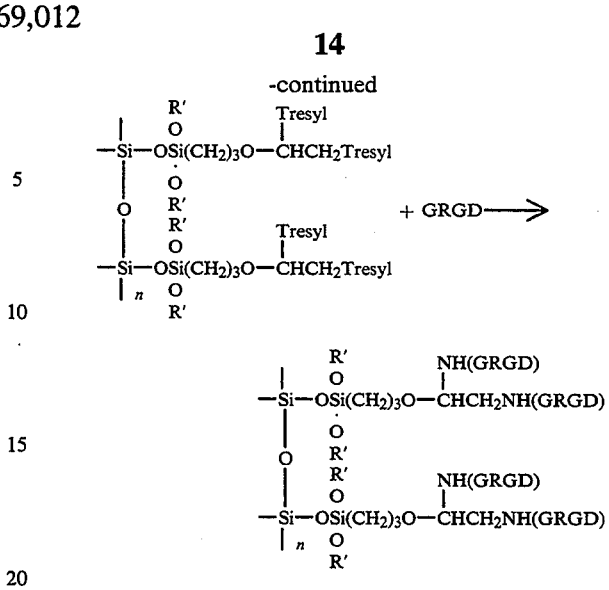

As an alternative example, the membrane of Example 1 is coupled to the ethyleneglycophosphorylcholine using dichlorodimethylsilane. First, the phosphorylcholine is reacted at with the dichlorodimethylsilane in anhydrous tetrahydrofuran (THF) using excess silane for 1 hr at 25° C. to prepare a chlorosilane/phosphorylcholine intermediate. Next, the intermediate product is recovered by evaporating the solvent and excess unreacted silane. The intermediate is then reacted with the Example 1 membrane in dry THF also at 25° C. for 16 hrs with stirring to complete the graft reaction.

Example 5

In this reaction, a compatibilizing polymer segment is grafted to the surface glycidyl functionality of the membrane of Example 2.

A poly(vinyl alcohol) segment is grafted to the membrane by reaction in water at 25° C. for 16 hrs with stirring. Reaction pH is 4.5–5.5. Further details regarding the optimized surface loading (# of grafts) and molecular weight distribution of the polymer with respect to a particular application may be found in the article by Y. Ikada mentioned previously.

Example 6

A tetrapeptide glycine-arginine-glycine-asparagine (GRGD) containing the cell adhesion sequence arginine-glycine-asparagine (RGD) is grafted to the surface of the membrane of Example 2. Tresyl chloride is used as a second coupling agent as follows:

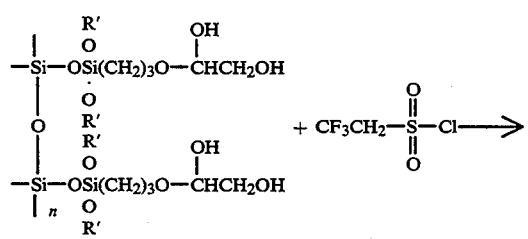

The glycidyl functionalized membrane from Example 2 is initially hydrolyzed in dilute acid (pH of about 2) by stirring for 2 hrs at 25° C. The hydrolyzed glycidyl groups are reacted with tresyl chloride in dry ether. The membrane is contacted with a 1.0 wt. % ether solution of the tresyl chloride at 25° C. for 15 min then rinsed with 0.2M bicarbonate buffer solution having a pH of 10. In fresh buffer solution, the tresyl chloride functionalized membrane is reacted with the peptide for 20 hrs at 25° C. The peptide sequence is attached at the terminal amino functionality on the glycine unit.

Example 7

In the following example, a vascular prosthesis is initially made according to Example 6 except that the SILON substrate has the form of a small bore tube. In the atomic oxygen treating first step, the outside surface of the tube is made hydrophilic to ½ of the wall thickness. Arterial endothelial cells are cultured on the treated surface to form a closely compatibilized article which is suitable for implant into a patient suffering advanced arteriosclerosis.

Example 8

A vascular prosthesis is made according to Example 7 except that the tubular silicone substrate has a microporous form made by a replamineform casting procedure described in Stimpson above which is hereby incorporated herein by reference.

Example 9

In the following example, an ELISA serological immune diagnostic technique is conducted using a 2.5 cm diameter, 100 μm thick SILON membrane treated with a uniform dose of atomic oxygen according to the procedure of Example 1 so that one side is hydrophilic and the other remains hydrophobic. The direct sandwich method is used.

The membrane is placed hydrophilic side down on a glass petri dish and a drop of antiserum containing a polyclonal anti-IgG antibody obtained as a 1 μl concentration from Sigma Corp. of St. Louis is placed on the membrane and allowed to dry. Next, absorbent tissue paper is placed under the membrane hydrophilic side and a drop of a test serum containing complementary antigens is placed over the antibodies. The complementary antigens adhere to the anti-IgG antibodies and excess fluid is absorbed through the membrane into the tissue paper. Using fresh absorbent tissue paper in a fresh petri dish, a second drop of antiserum containing 1 part complementary anti-IgG antibodies per 2000 parts water is placed over the antibody-antigen combination except that these second antibodies are conjugated to an enzyme alkaline phosphatase. Adherence of these additional antibodies to the antigens mark the antigens with the enzyme. Excess liquids diffuse through the membrane and are absorbed by the paper. Using fresh tissue paper in a fresh petri dish, a drop of phosphatase-reactive chromagen is placed over the membrane "sandwich." Since phosphatase marked antigens are present, a black chromagen-phosphatase product forms. Excess fluid is drawn through the membrane and is absorbed leaving the black colored "sandwich." The modified membrane allows waste liquids to be absorbed away from the test area for easy disposal.

Example 10

In the following example, time required to differentiate the growth rate of normal cells from malignant cells in a tissue biopsy is determined using a hydrophilic modified membrane of the present invention. The membrane has a surface wherein a plurality of hydrophilic surface areas are separated by a hydrophobic boundary so that each hydrophilic area is an isolated microculture.

The test is undertaken using a 2.5 cm diameter, 100 $\mu$m thick SILON membrane exposed to a uniform dosage of atomic oxygen according to Example 1, except that the membrane is masked during the atomic oxygen treatment. The mask gives the membrane a surface feature wherein hydrophilic areas of about 200 $\mu m^2$ are bounded by similarly sized hydrophobic regions in a checkerboard manner. The treated membrane is placed in a petri dish. The biopsy cells are serially diluted with cell culture media so that there will be about 0.7 cells per 200 $\mu m^2$ membrane area in the culture and the growth solution containing the cells is then added to the dish.

After one week, observation of the growth area under a microscope indicates that malignancy growth evaluation may be made in one tenth the time ordinarily required using 0.25 $cm^2$ size cultures in the prior art methods. Likewise, only one tenth the amount of culture materials is required.

Example 11

In the following example, a modified membrane of the present invention is used to separate a cultured product comprising cell growth differentiation factors from the cells without lysis.

Normal human primary cells taken from a surgical section are cultured in a petri dish having a modified membrane partition. $CO_2$ incubation conditions are used to produce cell growth differentiation factors wherein the cell are polarized by a 2.5 $cm^2$ SILON diffusion membrane which is 100 $\mu$m thick. The membrane is treated on both sides with a uniform dose of atomic oxygen according to the procedure of Example 1. One membrane side is hydrophilic and the other remains hydrophobic except for a horizontal hydrophilic line made by masking the treated surface. In the culture, the cells are added to the partition side having the linear hydrophilic area bounded by the hydrophobic area and growth media is added to the other side of the membrane having the hydrophilic surface. The cells polarize as a matter of course upon adherence to the hydrophilic "line" so that a distinct basal cell wall is formed adhered to the membrane as well as an opposite apical cell wall. In the course of the culture, nutrients diffuse across the membrane to replenish the cell growth media and the cell growth differentiation factors produced by the cultured cells are secreted by the basal cell wall and migrate through the membrane partition. After 30 days, the confluency in the opposite compartment is greater than 10 picomoles of the growth differentiation factors.

Example 12

In the following example, a modified membrane can be used to allow continual replenishment of nutrients to a cell culture. A petri dish culture is partitioned by modified membrane as described in Example 11 except that the SILON membrane is treated with atomic oxygen so that one side is hydrophilic and the other remains hydrophobic. The hydrophilic side forms the nutrient compartment and the cells are cultured in growth media adjacent the hydrophobic side. As nutrients in the growth medium are used by the cells, replenishing nutrients diffuse from the nutrient compartment to the cells compartment through the membrane.

The foregoing description of the invention is illustrative and explanatory thereof. Various changes in the materials, apparatus, and particular parts employed will occur to those skilled in the art. It is intended that all such variations within the scope and spirit of the appended claims be embraced thereby.

What is claimed is:

1. An organic polymer membrane having first and second opposing surfaces, wherein said first surface is hydrophilic and has an adjacent absorbent layer and said second surface is hydrophobic and contains adhered antibodies, said hydrophilic surface is prepared by a method comprising:

exposing a hydrophobic exterior surface of said membrane to a dosage of atomic oxygen or hydroxyl radicals at a temperature below about 40° C., said dosage being sufficient to form said hydrophilic surface having a uniform surface layer of hydrophilic functional hydroxyl groups, wherein said dosage is generated by a flowing afterglow microwave discharge and said surface is outside of a plasma produced by said discharge, wherein said surface exposed to said dosage has a depth of from about 50 to about 5000 angstroms and said dosage over said surface is within about 10 percent of an average dosage.

2. An organic polymer membrane having a surface comprised of a plurality of hydrophilic regions bounded by adjacent hydrophobic regions, said hydrophilic regions containing adhered cells at a maximum density of one cell per each hydrophilic region and said hydrophobic regions are substantially free of adhered cells, said hydrophilic regions having a uniform surface layer of hydrophilic functional hydroxyl groups created by exposing an exterior hydrophobic surface of said membrane at a temperature below about 40° C. to a dosage of atomic oxygen or hydroxyl radicals, said dosage being generated by a flowing afterglow microwave discharge and said surface being outside of a plasma produced by said discharge, wherein said exterior surface exposed to said atomic oxygen has a depth of from about 50 to about 5000 angstroms and said dosage over said surface is within about 10 percent of an average dosage.

3. The membrane of claim 2 wherein said hydrophilic regions are grafted with a compatibilizing compound selected from the group consisting of phosphorylcholines, peptides, lipids, proteins, nucleic acids, poly(ethylene oxide), poly(vinyl alcohol) and acyl terminated upper alkyl radicals.

4. The membrane of claim 3 wherein said compound is selected from the group consisting of one or more phosphorylcholines, peptides, lipids, proteins, and nucleic acids.

5. The membrane of claim 3, wherein said compatibilizing compound is selected from the group consisting of poly(vinyl alcohol) and poly(ethylene oxide).

6. The membrane of claim 2 in the form of a tube.

7. An assay method using a permeable organic polymer membrane having a hydrophilic surface formed opposite a hydrophobic surface, said hydrophilic surface having a uniform surface layer of hydrophilic functional hydroxyl groups created by exposing an exterior hydrophobic surface of said membrane at a temperature below about 40° C. to a dosage of atomic oxygen or hydroxyl radicals, said dosage being generated by a flowing afterglow microwave discharge and said surface being outside of a plasma produced by said discharge, wherein said surface exposed to said atomic oxygen has a depth of from about 50 to about 5000 angstroms and said dosage over said surface is within about 10 percent of an average dosage, said assay comprising the steps of:
  (a) adhering known antibodies to said hydrophobic surface;
  (b) placing said hydrophilic surface in contact with an adjacent absorbent material;
  (c) covering said antibodies with a test solution, wherein antigens specific to said antibodies adhere thereto to form an antibody-antigen complex and non-adhered antigens migrate to said hydrophilic surface and are absorbed by said absorbent material;
  (d) covering said hydrophobic surface with a solution of said antibodies conjugated to an indicating enzyme, wherein said conjugated antibodies and said antigen-antibody complex form an antibody-antigen-antibody/enzyme complex and excess fluid is absorbed by said absorbent material; and
  (e) developing said antibody-antigen-antibody/enzyme complex with a solution of developing compound reactive with said enzyme to indicate presence of said antibody-antigen-antibody/enzyme complex as a positive result or an absence of said complexes as a negative result, wherein excess developing solution is absorbed by said absorbent material.

8. A cell culturing method using a permeable organic polymer membrane having a hydrophilic surface comprising a plurality of hydrophilic regions bounded by adjacent hydrophobic regions, said hydrophilic regions having a uniform surface layer of hydrophilic functional hydroxyl groups created by exposing an exterior hydrophobic surface of said membrane at a temperature below about 40° C. to a dosage of atomic oxygen or hydroxyl radicals, said dosage being generated by a flowing afterglow microwave discharge and said surface being outside of a plasma produced by said discharge, wherein said exterior surface exposed to said atomic oxygen has a depth of from about 50 to about 5000 angstroms and said dosage over said surface is within about 10 percent of an average dosage, said cell culturing method comprising the steps of:
  (a) distributing a group of cells on said membrane in a growth medium, wherein said cells adhere to said hydrophilic regions at a maximum density of one cell per each hydrophilic region and said hydrophobic regions are substantially free of adhered cells;
  (b) growing said cells on said membrane; and
  (c) obtaining a count of malignant cells growing on said membrane.

9. A cell culturing method using a permeable organic polymer membrane having first and second opposing surfaces, said first surface comprising a hydrophilic region bounded by a hydrophobic region, said hydrophilic region having a uniform surface layer of hydrophilic functional hydroxyl groups created by exposing an exterior hydrophobic surface of said membrane at a temperature below about 40° C. to a dosage of atomic oxygen or hydroxyl radicals, said dosage being generated by a flowing afterglow microwave discharge and said surface being outside of a plasma produced by said discharge, wherein said exterior surface exposed to said atomic oxygen has a depth of from about 50 to about 5000 angstroms and said dosage over said surface is within about 10 percent of an average dosage, second said cell culture method comprising the steps of:
  (a) forming cell culturing and product compartments on opposite sides of said membrane, wherein said first membrane surface is adjacent to said cell culturing compartment and said second membrane surface is adjacent to said product compartment, said cell culturing compartment comprising cells in a growth medium, said cells having a gene for expression of a desired product;
  (b) inducing said cells to adhere to said hydrophilic region of said first surface of said membrane, wherein said cells polarize with a basal cell wall adjacent said first surface; and
  (c) inducing migration of said nutrient from said nutrient compartment to said cells compartment by maintaining nutrient in said cell culturing compartment, wherein said cells absorb said nutrient and in response thereto secrete a product preferentially through said basal cell wall and said membrane into said product compartment.

10. A cell culturing method using a permeable organic polymer membrane, said membrane having first and second opposing surfaces, said first surface comprising a hydrophilic surface and said second surface comprising a hydrophobic surface, said hydrophilic surface having a uniform surface layer of hydrophilic functional hydroxyl groups created by exposing an exterior hydrophobic surface of said membrane at a temperature below about 40° C. to a dosage of atomic oxygen or hydroxyl radicals, said dosage being generated by a flowing afterglow microwave discharge and said surface being outside of a plasma produced by said discharge, wherein said exterior surface exposed to said atomic oxygen has a depth of from about 50 to about 5000 angstroms and said dosage over said surface is within about 10 percent of an average dosage, said cell culture method comprising the steps of:
  (a) forming a nutrient compartment and a cells compartment on opposite sides of said membrane, wherein said first surface is adjacent said nutrient compartment and said second surface is adjacent to said cells compartment, said nutrient compartment comprising a solution of nutrient and said cells compartment comprising cells in a growth medium; and
  (b) inducing migration of said nutrient from said nutrient compartment to said cells compartment by maintaining a higher concentration of said nutrient in said nutrient compartment.

* * * * *